United States Patent [19]

Frankel et al.

[11] 4,406,718

[45] Sep. 27, 1983

[54] TETRAAZIDO POLYESTERS AND METHODS OF PREPARATION

[75] Inventors: Milton B. Frankel, Tarzana; Edgar R. Wilson, Glendale; Joseph E. Flanagan, Woodland Hills, all of Calif.

[73] Assignee: The United States of America as represented by the Secretary of the Navy, Washington, D.C.

[21] Appl. No.: 283,708

[22] Filed: Jul. 16, 1981

[51] Int. Cl.³ .................... C06B 25/18; C07C 117/00
[52] U.S. Cl. .................... 149/96; 149/19.1; 149/19.8; 260/349
[58] Field of Search .............. 149/96, 19.1, 19.8; 260/349

[56] References Cited

U.S. PATENT DOCUMENTS

| | | | |
|---|---|---|---|
| 3,873,579 | 3/1975 | Rosher | 260/349 |
| 4,085,123 | 4/1978 | Flanagan et al. | 260/349 |
| 4,141,910 | 2/1979 | Flanagan et al. | 260/349 |
| 4,268,450 | 5/1981 | Frankel et al. | 260/349 |

OTHER PUBLICATIONS

Wertheim, Textbook of Organic Chemistry, 3rd Ed., McGraw-Hill Book Co., New York, 1951, p. 217.

*Primary Examiner*—Leland A. Sebastian
*Attorney, Agent, or Firm*—R. S. Sciascia; A. L. Branning; J. C. LaPrade

[57] ABSTRACT

Novel tetraazido polyesters comprising compounds of the following generic formula

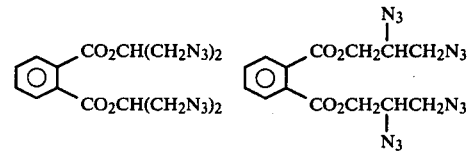

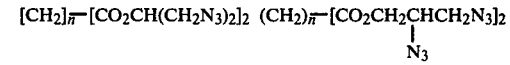

and methods of preparation of these polyesters.

11 Claims, No Drawings

TETRAAZIDO POLYESTERS AND METHODS OF PREPARATION

BACKGROUND OF THE INVENTION

This invention generally relates to the preparation and use of tetraazido polyesters. Solid propellants, gun propellants, and explosives are generally composed of oxidizers, binders, plasticizers, and sometimes a fuel. The oxidizers such as ammonium perchlorate and HMX are well known to the art. Hydrocarbon binders and inert plasticizers such as dioctyl phthalate, and triacetin are generally used. Recently, attempts have been made to replace the inert plasticizers with energetic materials so as to increase the overall energy of the propellant.

Organic high nitrogen compounds are useful ingredients of solid propellants for guns, rockets, and gas generator compositions. Their main combustion product is nitrogen, which is an extremely stable molecule that shows little tendency to react even at the high temperatures that exist in gun tubes and rocket engines. Additionally, nitrogen is completely transparent in the infrared and so contributes no interference to missile guidance systems using infrared radiation.

One way of making a compound high in nitrogen is to introduce several azido ($N_3$) groups into the molecule. The most attractive feature of azido compounds is their high heats of formation. The azido groups contributes a positive heat of formation of about 85 kcal/unit. This high contribution of the azido group to the heat of formation is most clearly evident from a comparison of ethanol and 2-azidoethanol. The heat of formation of ethanol is $-66$ keal/mole, while 2-azidoethanol has a heat of formation of $+22.5$ keal/mole. The heat of formulation of the tetraazido polyesters is equally high. Thus, the energy content of azido compounds is readily evident. The key to the practical utilization of azido compounds is to tailor their molecular structure to take advantage of the high energy content of the azido moeity and still have acceptable properties in terms of insensitivity and good thermal stability.

The simplest composition contemplated by this invention is merely a mixture of a tetraazido polyester and nitrocellulose. A composition such as this when used as a gun propellant serves to increase impetus without increasing the flame temperature significantly by virtue of the fact that this composition produces more gas per unit weight on decomposition than a typical double-base composition of nitrocellulose-nitroglycerin propellant.

OBJECTS OF THE INVENTION

It is one object of the invention to provide a novel tetraazido polyester that has utility as an ingredient for gun propellants.

It is another object of the invention to provide a novel method of preparing a tetraazido polyester.

Another object of the present invention is to provide a propellant binder with low sensitivity.

A further object of the present invention is to provide an explosive with excellent thermal and chemical stability at a low sensitivity.

A still further object of the present invention is to synthesize a tetraazido polyester.

It is, also an object of the present invention to provide a propellant binder with excellent mechanical properties and a high energy content.

Another object of the present invention is to provide a propellant binder with excellent thermal and chemical stability.

SUMMARY OF THE INVENTION

This invention relates to a tetraazido polyester and to a process for their preparation. Compounds containing one or more azido groups are useful as energetic plasticizers for gun propellants, solid propellants, and explosives. This invention provides a novel class of polyazido compounds having utility as stated above, and also provides a novel process for their preparation. The novel azido compounds of the invention are the polyazidoalkyl and polyazidoaryl esters which are represented by the formulas:

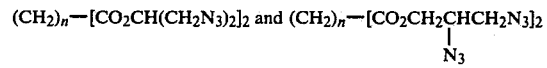

where n varies from 0 to 10 but is usually in the range of 2 to 4, and the formula:

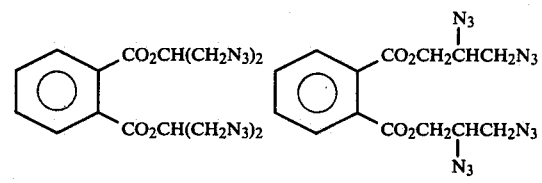

DESCRIPTION OF THE PREFERRED EMBODIMENT

The tetrazido polyesters depicted above are prepared by the esterification of aliphatic and aromatic di-acid chlorides with diazidoalkanols.

Among the preferred diazidoalkanols are
1,3-diazido-2-propanol,
2,3-diazido-1-propanol Other diazido alcohols can be substituted.

Among the di-acid chlorides that can be used are adipyl chloride, phthaloyl chloride.

The following examples are intended only to illustrate the invention and they are in no way to be considered as limitative of the inventive concept.

EXAMPLE I

Preparation of bis(2,3-diazidopropyl)adipate 8.52 g (0.06 Mole) 2,3-diazidopropanol in 20-ml dry $CCl_4$ is added dropwise to 5.49 g (0.03 Moles) adipyl chloride in 30-ml dry $CCl_4$ while the temperature is held below 20° C. At the end of the addition, the cooling bath is removed and the temperature is allowed to rise to 25° C. The reaction mixture is allowed to stir at ambient temperature for 18 hours under a slow flow of nitrogen to purge HCl produced in the reaction. At the end of this period the reaction mixture is washed with $H_2O$, dilute bicarbonate solution, and a final $H_2O$ wash. The resultant colorless solution is stripped of solvent to yield 9.8 g (83%) colorless oil $n_D{}^{25}$ 1.5050, $d_4{}^{25}$ 1.258; infrared spectrum is consistent with the expected structure. Elemental analysis for nitrogen gives 42.01%, theoretical is 42.62%.

EXAMPLE 2

Preparation of bis(2,3-diazidopropyl)-o-Phthalate 2.84 g (0.02 Moles 2,3-diazidopropanol and 1.58 g (0.02 Mole) pyridine in 10-ml dry CCl$_4$ is added dropwise to 2.03 g (0.01 Mole) phthaloyl chloride in 10-ml dry CCl$_4$. Temperature is held at 20°–30° C. by means of ice bath. At the end of the addition, the reaction mixture is allowed to stir at ambient temperature for one hour, then is refluxed for 1 hour. Following cooling, the reaction mixture is washed with H$_2$O dried and stripped to yield 3.3 g of oil (80.5%), n$_D$$^{25}$ 1.5516, d$_4$$^{25}$ 1.315. Infrared spectrum is consistent with the expected structure. Elemental analysis for nitrogen gives 40.02%, theoretical is 40.57%.

EXAMPLE 3

Preparation of bis(1,3-diazidoisopropyl) Adipate 8.52 g (0.06 Mole) 1,3-diazido-2-propanol and 4.74 g (0.06 Mole) pyridine in 25-ml CH$_2$Cl$_2$ are added dropwise to 5.49 g (0.03 Mole) adipyl chloride in 25-ml CH$_2$Cl$_2$ at 15°–20° C. Pyridine hydrochloride precipitates immediately. When the addition is complete, the reaction mixture is allowed to stir at ambient temperature for 18 hours. Following this, the reaction mixture is washed with H$_2$O, dilute bicarbonate solution, and H$_2$O again. The resultant solution is passed through a neutral alumina column and treated with decolorizing charcoal and finally stripped to yield 6.4 g (54%) colorless oil. n$_D$$^{25}$ 1.5014, d$_4$$^{25}$ 1.254. Infrared spectrum is consistent with the expected structure. Elemental analysis for nitrogen gives 41.96%, theoretical is 42,62%.

EXAMPLE 4

Preparation of bis(1,3-diazidoisopropyl)-o-Phthalate 29.0 g (0.204 Mole) 1,3-diazido-2-propanol and 15.8 g (0.20 Mole) pyridine in 50-ml CH$_2$Cl$_2$ is added dropwise to 20.3 g (0.10 Mole) phthaloyl chloride in 50-ml CH$_2$Cl$_2$ at 15°–20° C. Following the addition, the reaction mixture was allowed to warm to ambient temperature and stirred for one hour. The reaction mixture was then refluxed for four hours. The resultant orange solution was washed with H$_2$O, dilute bicarbonate solution, and again with H$_2$O, and finally stripped to yield 40 g (97%) orange oil. The oil was dissolved in 50-ml CCl$_4$ and passed through a silica-gel column and treated with decolorizing charcoal. The resultant colorless solution was stripped to yield 19 g (46%) faintly colored oil. n$_D$$^{25}$ 1.5498, d$_4$$^{25}$ 1.314. Infrared spectrum is consistent with the expected structure.

To those skilled in the art, many modifications and variations of the present invention are possible in light of the above teachings. It is therefore to be understood that the present invention may be practiced otherwise than as specifically described herein and still be within the spirit and scope of the appended claims.

We claim:

1. A tetraazido polyester of the formula:

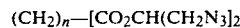

where n varies from 2 to 10.

2. A gun propellant comprising nitrocellulose and a tetraazido polyester of the formula:

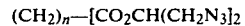

where n varies from 2 to 10.

3. A tetraazido polyester of the formula:

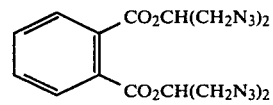

4. A gun propellant comprising nitrocellulose and a tetrazido polyester of the formula:

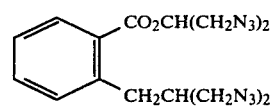

5. Bis(2,3-diazidopropyl)adipate.
6. Bis(2,3-diazidopropyl)-o-phthalate.
7. Bis(1,3-diazidoisopropyl)adipate.
8. A tetraazido polyester of the formula:

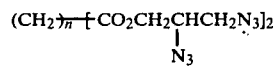

where n varies from 2 to 10

9. A method of preparing the tetraazido polyester of claim 8 comprising the steps of reacting an aliphatic diacid chloride with a diazidoalkanol in a liquid diluent at a temperature ranging from 10¼C. to 100¼C.

10. A tetraazido polyester of the formula:

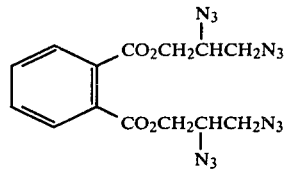

11. A method of preparing the tetraazido polyester of claim 10 comprising the steps of reacting an aromatic diacid with a diazidoalkanol in a liquid diluent at a temperature in the range of 10¼C. to 100¼C.

* * * * *